US006767330B2

United States Patent
Lavery et al.

(10) Patent No.: US 6,767,330 B2
(45) Date of Patent: Jul. 27, 2004

(54) FOOT TEMPERATURE AND HEALTH MONITORING SYSTEM

(75) Inventors: Lawrence A. Lavery, San Antonio, TX (US); C. Mauli Agrawal, San Antonio, TX (US); Kyriacos A. Athanasiou, Houston, TX (US); George P. Constantinides, San Antonio, TX (US); Dan R. Lanctot, San Antonio, TX (US); Ruben G. Zamorano, San Antonio, TX (US)

(73) Assignee: Salix Medical, Inc., San Antonio, TX (US)

( * ) Notice: Subject to any disclaimer, the term of this patent is extended or adjusted under 35 U.S.C. 154(b) by 152 days.

(21) Appl. No.: 10/029,043

(22) Filed: Dec. 20, 2001

(65) Prior Publication Data

US 2002/0082486 A1 Jun. 27, 2002

Related U.S. Application Data

(63) Continuation-in-part of application No. 09/578,948, filed on May 25, 2000, now Pat. No. 6,398,740.

(51) Int. Cl.⁷ .............................. A61B 5/00; A61B 6/00
(52) U.S. Cl. ...................... 600/549; 600/474; 600/300; 128/920
(58) Field of Search ................................ 600/300–301, 600/474–477, 473, 547, 549, 554–557, 587, 592, 594; 128/897, 898, 920; 340/573.1; 73/172

(56) References Cited

U.S. PATENT DOCUMENTS

| | | | | |
|---|---|---|---|---|
| 4,379,461 A | * | 4/1983 | Nilsson et al. | 600/474 |
| 5,642,096 A | * | 6/1997 | Leyerer et al. | 340/573.1 |
| 6,080,106 A | * | 6/2000 | Lloyd et al. | 600/300 |
| 6,090,050 A | * | 7/2000 | Constantinides | 600/549 |
| 6,290,646 B1 | * | 9/2001 | Cosentino et al. | 600/300 |
| 6,322,504 B1 | | 11/2001 | Kirshner | |
| 6,440,084 B1 | * | 8/2002 | Gentempo et al. | 600/549 |

* cited by examiner

Primary Examiner—Max F. Hindenburg
Assistant Examiner—Michael Astorino
(74) Attorney, Agent, or Firm—Jenkens & Gilchrist, PC

(57) ABSTRACT

The present invention provides an apparatus and method for monitoring skin temperatures at predetermined locations on the body of a human or an animal. One embodiment includes a platform with a grid including holes on which the user stands. Under the grid is a movable array of light sensors and temperature sensors. The foot position is determined from the output of the light sensors. The temperatures at predetermined locations on the skin surface are determined by the signals obtained from the temperature sensors. Additional vital health information may be obtained by other sensors on the apparatus. The data may be stored for future retrieval, or transmitted to a remote location for off-site monitoring. Alternative embodiments include sensor blankets or wraps whereby temperature sensors monitor skin temperature for areas of pressure on the blanket or areas covered by the wrap.

30 Claims, 4 Drawing Sheets

FOOT TEMPERATURE AND HEALTH MONITORING SYSTEM

This is a continuation-in-part of U.S. Pat. No. 6,398,740, filed on May 25, 2000.

FIELD

The present invention pertains to a monitoring apparatus; more particularly, the present invention pertains to an apparatus and method for monitoring the skin temperatures of animals at different predetermined locations together with other vital information indicative of the health of a human being.

BACKGROUND

Many conditions which have a negative impact on the health of animals, to include human beings, are preceded by small changes in skin temperature, together with slight changes in weight or blood pressure. For example, a significant weight gain may be indicative of fluid retention. And fluid retention, when accompanied by an increase in blood pressure, may be predictive of the onset of congestive heart failure.

Afflictions, particularly ulcerations, can be predicted by a change in skin temperatures. Specifically, the skin temperature on the bottom of the feet can be predictive of foot problems such as ulcerations. In the United States alone, it is estimated that up to 16,000,000 people suffer from diabetes; and approximately 60–70% of these diabetics will eventually develop foot-related medical problems sometime during their lifetime. Of all diabetes-related hospitalizations, 20% of these hospitalizations are for foot-related medical problems. The number of hospitalizations for foot-related medical problems, such as sores that will not heal, can be reduced if medical personnel are forewarned of significant changes in the skin temperatures on the bottom of the feet. For example, it is well known that skin temperatures on the bottom of a person's feet will increase before a visible ulceration appears.

Afflictions that cause tissue inflammation and injury, such as tendon injuries and fractures, ulcers in persons with neuropathy or who are bedridden, can be predicted or identified by subtle changes in skin temperatures. For instance, in diabetics with neuropathy elevated skin temperatures on the sole of the foot can help medical personnel identify areas prone to ulceration or fracture. For patients who are bedridden, elevated skin temperatures can help identify specific areas on the heels, buttocks or sacrum that are injured, inflamed and are at the early stages of developing a decubitus ulceration or pressure sore. The capability of identifying locations prone to ulcerations is particularly helpful for persons with diminished cognitive function or who are so debilitated that they do not have verbal skills to provide information to their care-givers. Such patients may include those with spinal cord injury or stroke victims.

Foot problems are particularly problematic for diabetics because diabetics often lose sensation in their feet. This loss of sensation often leads to a foot fracture (Charcot) or a skin ulceration caused by friction and pressure. In extreme cases the ulceration, if not caused to heal properly, may eventually lead to an amputation of a diabetic's foot. The foot problems typically associated with diabetic peripheral neuropathy include numbness or insensitivity to pain or temperature, tingling, burning, or prickling, sharp pains or cramps, extreme sensitivity to touch, and loss of balance and coordination. Such pain and suffering significantly diminishes the quality of life of a diabetic. In addition, foot-related medical problems substantially increase the diabetic's health care cost.

There is therefore a need in the art for a device and system which facilitates the monitoring of skin temperatures. For diabetics particularly, there is a need in the art for a device and system which will monitor skin temperatures on the bottom of a patient's feet and provides an early warning of any significant temperature differences in skin temperatures between common areas of the two feet or between neighboring sites. Such foot skin temperature monitoring may provide an early indication of conditions which can lead to ulceration, infection, wound healing problems, fracture, and even amputation.

In yet another important area for diabetics, changes in blood pressure at various locations on the human body may be indicative of reduced blood flow. Such reduced blood flow may lead to significant reduction in the health of the affected body part. Another important area of observation for diabetics would be changes in blood chemistry which may be indicative of nascent problems which are not yet symptomatic. Coupling this information together with foot skin temperatures would create an extremely powerful tool for diagnosticians.

The ability to monitor skin temperatures at predetermined areas can also be expanded to use in animals such as race horses. By serial temperature monitoring, areas prone to injury can be identified and treated before a career-ending or catastrophic injury. This methodology can also be used to evaluate and monitor the effectiveness of treatment in those animals since they are obviously unable to communicate to their veterinarian about the severity or location of the pain.

Thus, there is a significant need to develop a device to facilitate the monitoring of skin temperature at predetermined areas together with other vital health information such as weight, blood pressure, and blood glucose levels. Such monitoring of other vital information, when coupled with skin temperature readings, may provide an early indication of pending serious health problems which, if treated early, can be substantially diminished or even avoided.

SUMMARY

The present invention facilitates the monitoring of skin temperatures at predetermined locations on a human's or animal's body to include the skin temperature on the bottom, side, or top of a person's foot. In an alternate embodiment, the disclosed invention couples skin temperature readings together with other important health indicators such as body weight and blood pressure. This monitoring of vital health information is accomplished by an apparatus which is built around a system for monitoring the skin temperature at different predetermined locations. For diabetics, these predetermined locations may be on the plantar, dorsal, medial, or lateral aspects of the contra-lateral feet.

In the disclosed preferred embodiment of the invention, a platform includes a moving array of light sensors and infrared temperature sensors positioned under a grid on which the patient stands. The light sensor portion of the moving array determines the position of the patient's feet on the grid. The infrared temperature sensors of the moving array determines foot skin temperatures as it travels under the grid. Holes in the grid allow each infrared temperature sensor to make numerous temperature measurements of the skin on the bottom of each foot. Once the foot skin temperatures have been taken through each hole in the grid covered by the patient's foot, the temperature measurements at each location can be transmitted to and stored in a computer memory. The computer memory may be located at the device itself, or the foot skin temperature data may be transmitted to a computer memory at a remote location using a built-in modem and a telephone connection or via wireless means.

If there is a significant difference between the skin temperatures on the bottom of the left foot and the bottom of the right foot, or a difference between adjacent points, an alarm signal can be provided to the user. The sensed skin temperatures can also be displayed to the user as a temperature reading, stored for future use, or sent to a central monitoring facility.

In another embodiment, force or pressure sensors co-located with the grid on which the patient stands may also be used to locate positions on the foot that will be measured with the temperature sensors. The patient's weight is measured by means of traditional force sensors located at each leg of the device. In still other embodiments, a blood pressure cuff and pulse monitor may be used. The blood pressure cuff may be placed at heart level on the user's arm or an additional pulse monitor cuff may be placed around the user's ankle or the user's toe. A further embodiment could monitor and transmit blood glucose levels.

Once vital health information has been sensed, that information may be compared to previously sensed vital health information. For example, a comparison of a patient's weight and blood pressure to prior readings may reveal a condition predictive of congestive heart failure.

All of the sensed vital health information may be displayed to the user and/or transmitted by telephone or other commonly used wireless communication systems to a central facility where medical professionals can determine if the sensed conditions are predictive of imminent medical problems. If desired, the apparatus itself may produce alarms of particularly dangerous conditions. For example, if the difference in the skin temperatures sensed on the bottom of the left foot and the bottom of the right foot or if the patient's blood pressure is above a certain level, an audible signal or a visual message can be generated, indicating an urgent need to consult with a medical professional.

In another embodiment, a blanket containing temperature sensors may be placed under a body part, particularly a body part which is most likely to develop a decubitus ulcer due to immobility. The apparatus may also be designed in the form of a wrap containing temperature sensors, which can be positioned around an extremity of a human being or animal in order to monitor the skin surface temperature of the body part contained therein.

BRIEF DESCRIPTION OF THE FIGURES

A better understanding of the apparatus and method for monitoring the temperature on the planar aspects of a human foot and other vital health information may be had by reference to the drawings, wherein.

DESCRIPTION OF THE EMBODIMENTS

Figure 1:
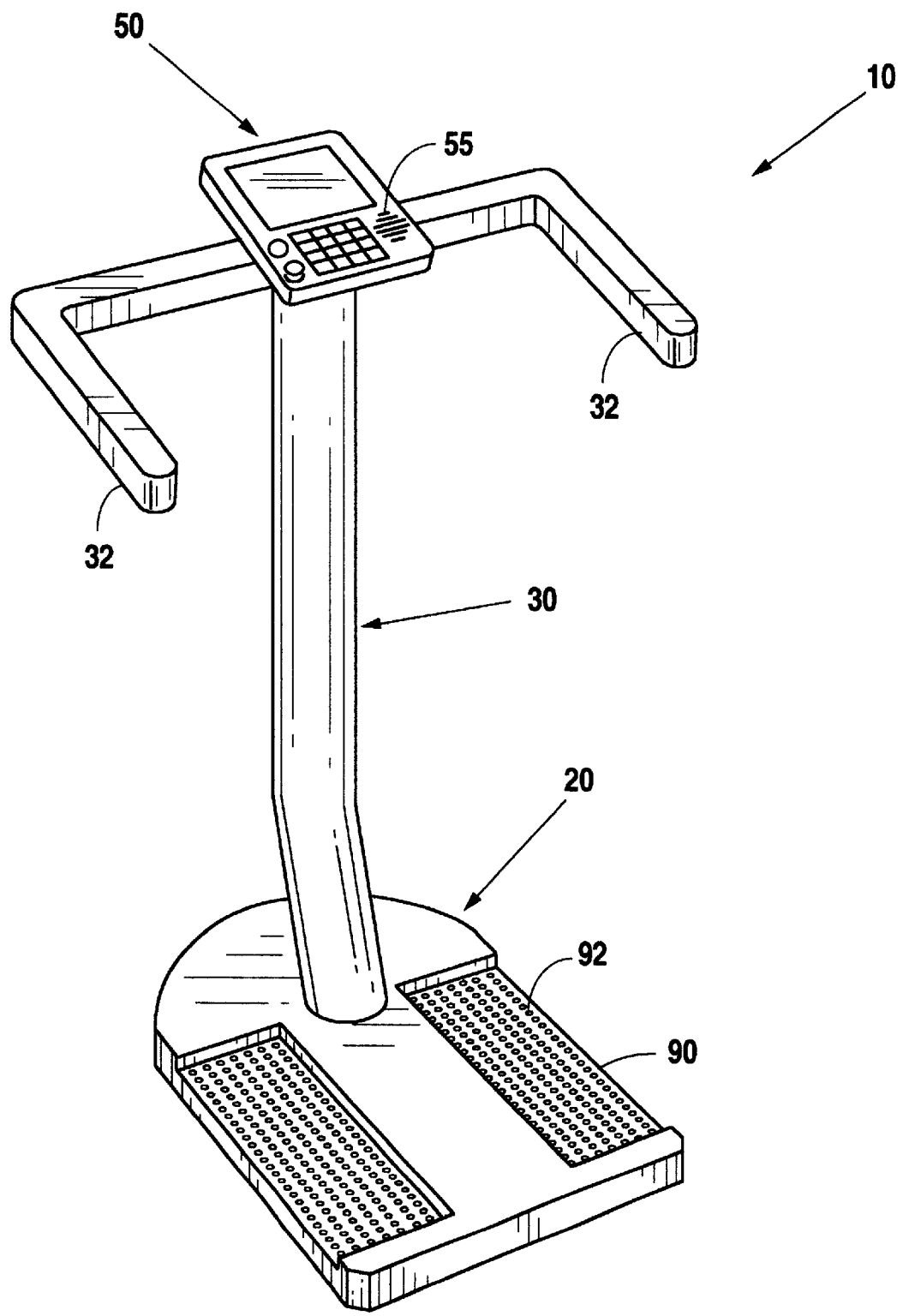
FIG. 1 is a perspective view of the preferred embodiment of the present invention.
Figure 1A:
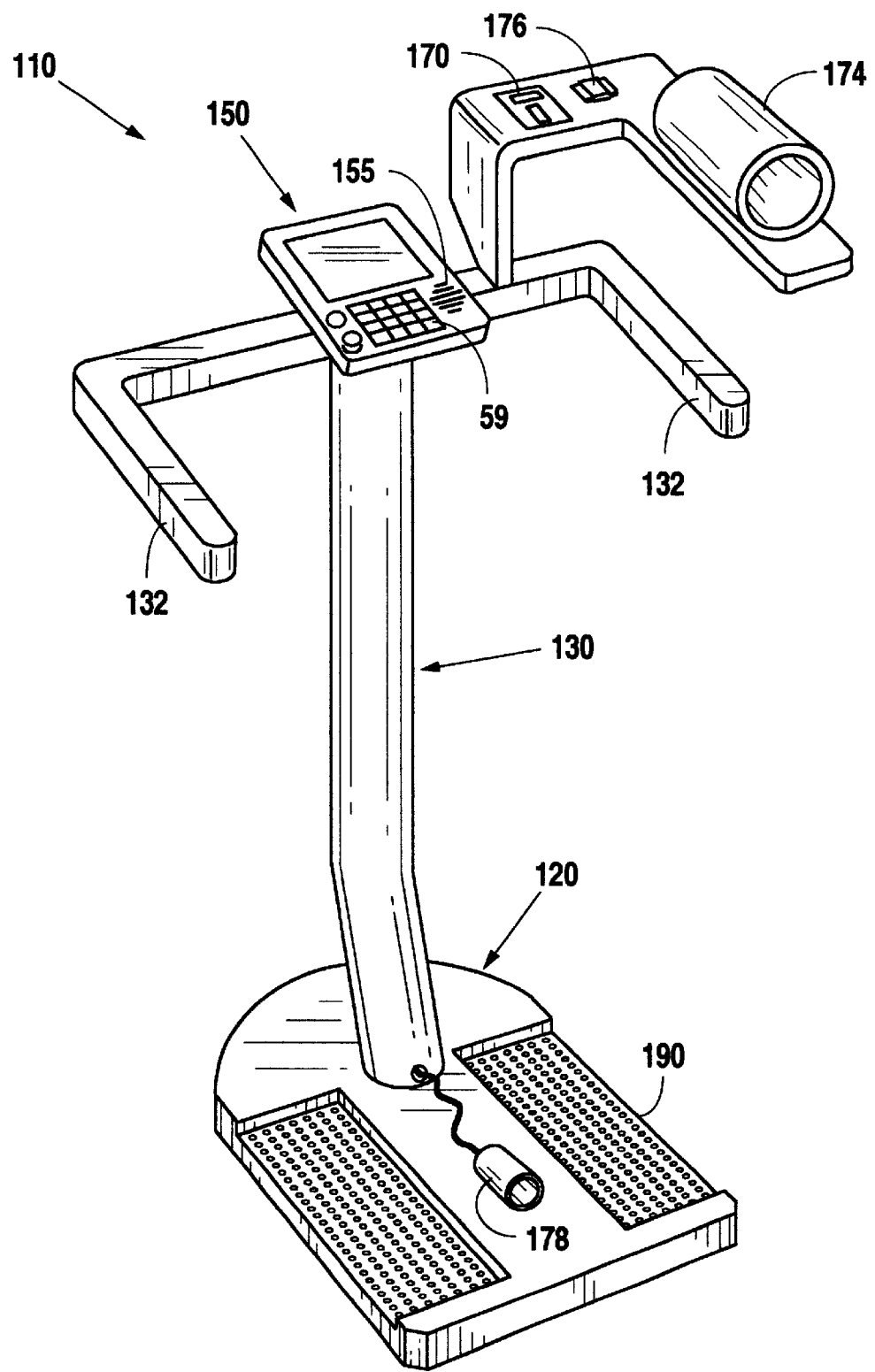
FIG. 1A is a perspective view similar to FIG. 1 illustrating the inclusion of additional features.

As may be seen in FIG. 1, the preferred embodiment of the invention 10 includes a platform assembly 20 on which the patient stands, a pedestal assembly 30, and a readout panel assembly 50. The pedestal assembly includes a pair of arms 32 which a patient may use for support when stepping on the platform assembly 20 and for mounting additional equipment as shown in FIG. 1A.

Figure 2:
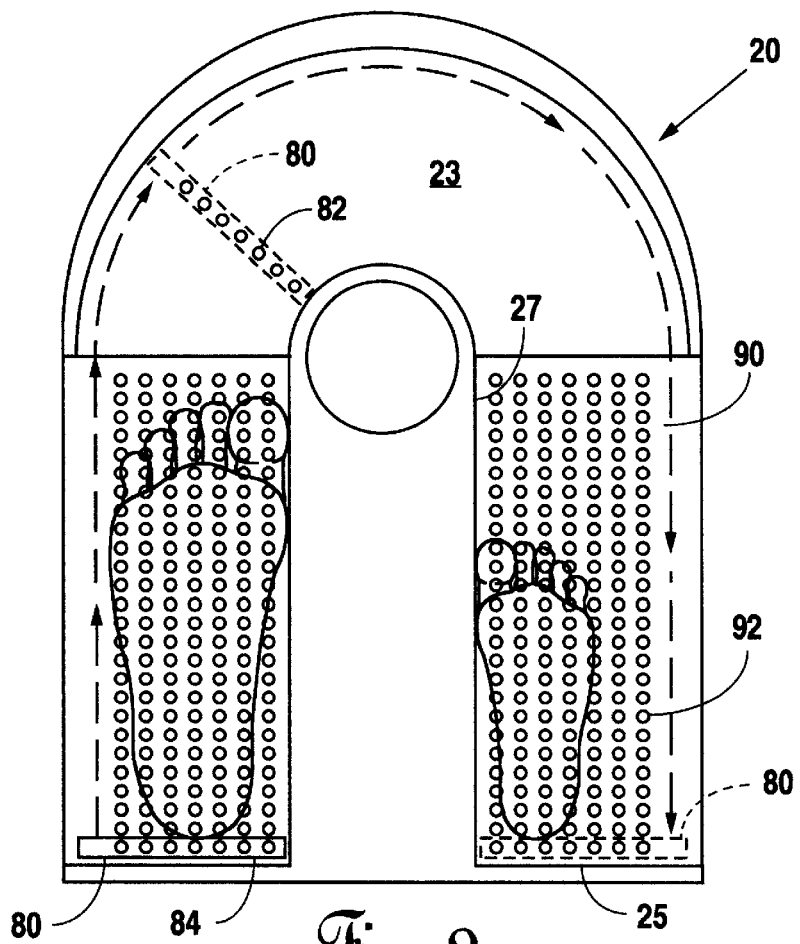
FIG. 2 is a top plan view of the platform which is used to measure the temperatures on the plantar aspects of the user's feet.

As may be seen in FIG. 2, the platform assembly 20 includes a movable substantially linear array 80 of infrared sensors 82 on a moving frame 84. In the embodiment shown in FIG. 2, the movable linear array 80 of infrared sensors includes seven sensors 82. Those of ordinary skill in the art will understand that the number of sensors 82 used in the linear array 80 is dependent on the number of locations on the bottom of the patient's foot at which a physician may request skin temperatures and the typical size of the patient's foot. The linear array 80 of infrared sensors 82 moves first under one foot and then under the other foot. Skin temperatures are taken through the holes 92 in a grid plate 90 on which the patient actually stands.

While a linear array 80 of infrared temperature sensitive sensors 82 is shown in the preferred embodiment, those of ordinary skill in the art will understand that other non-contact temperature sensing systems suitable for rapid sensing of temperatures at point locations may also be used.

As shown in FIG. 2, the linear array 80 of infrared sensors 82 begins its travel path on the left side of the platform assembly 20. To illustrate that the platform assembly is sized to accommodate a wide range of foot sizes, the linear array 80 of infrared sensors 82 is shown passing under a man's foot size 16E from heel to toe. Once the traverse of the foot on the left side of the platform assembly 20 is complete, the linear array 80 of infrared sensors 82 is guided on an arcuate path 23 to the patient's other foot on the right side. In FIG. 2, the other foot is shown as a woman's size 5A to indicate that a small foot size does not present any difficulties for the person using the device 10. Once the arcuate path 23 has been traversed, the linear array 80 of infrared temperature sensors 82 passes under the foot on the right side of the device 10 from toe to heel, taking skin temperature measurements along the bottom of the user's foot as it goes along.

Figure 2A:
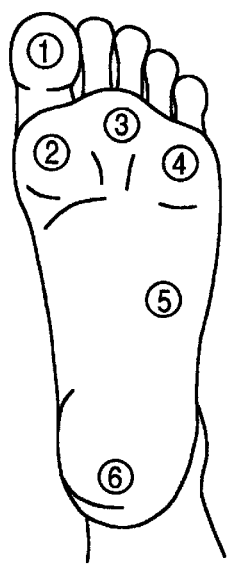
FIG. 2A is a bottom view of a patient's foot indicating typical locations used for sensing skin temperature.

Skin temperature measurements are available at all points at which there is an opening 92 in the grid 90 on the platform assembly 20. A complete array of such skin temperature readings may be used to produce complex diagrams of foot skin temperatures where colors are used to represent varying ranges of foot skin temperature. Alternatively, a physician may be interested in skin temperatures at specific predetermined locations on a patient's foot such as the ones shown in FIG. 2A. Where skin temperature readings at only predetermined locations are required, the computer receiving the skin temperature only selects those temperature readings at the predetermined locations such as shown in FIG. 2A for reporting purposes and disregards the remainder. For smaller feet, at least 50 discrete skin temperature measurements can be taken. For larger feet, up to 150 discrete skin temperature measurements can be taken. For those skilled in the art, an even higher number of discrete points may be assessed.

The movement of the linear array 80 of infrared sensors 82 is facilitated by a small motor located within the platform assembly 20 (not shown). Because of the arcuate movement or U-Turn taken by the linear array 80 of infrared sensors 82 at the top of the platform assembly 20, the same infrared sensor 82 measures the skin temperature at a predetermined location on each foot, thus minimizing any sensing error. For example, if the first infrared temperature sensor 82 in the linear array 80 measured the skin temperature on the bottom of the big toe in the left foot (location 1 in FIG. 2A), the same infrared temperature sensor would measure the skin temperature on the bottom of the big toe on the patient's right foot.

It is expected that the patients who would receive the greatest benefit from the disclosed apparatus are diabetics who are typically at high risk for developing medical complications on their lower extremities, particularly their feet.

In an alternate embodiment of the present invention 10 as shown in FIG. 1A, the patient may obtain a quick scan of the temperatures on the plantar aspects of both feet, body weight, and blood pressure. Items similar to those shown in FIG. 1 are designated by reference numbers including a 1 in the hundreds place.

The quick scan of foot temperatures allows the detection and monitoring of differences in skin temperatures between the bottom of the left foot and the bottom of the right foot or the monitoring of foot temperatures at different locations on the bottom of the patient's foot over time. Variations in foot skin temperatures often signal conditions which are predictive of inflammation or ulceration and which conditions, if left untreated, may lead to eventual amputation of an entire lower extremity.

As shown in FIG. 1 and FIG. 1A, the apparatus of the present invention 10, 110 is not unlike a commonly used bathroom scale for determining body weight. Specifically, the user is instructed to first step on the platform 20, 120. The location of the patient's foot is initially located by causing the heel to be placed against a first rear surface 25 and the medial aspect of the foot to be placed against a second surface 27 substantially perpendicular to the first rear surface 25. Further information concerning the location of the patient's foot may be determined by an array of pressure sensors (not shown) located in the platform assembly 120 or an array of optical light sensors (not shown) located in the platform assembly 20. Additional background light can be projected downward from the handles 32 of the apparatus 10 in order to clearly distinguish the outline of the patient's feet. In the disclosed embodiment, the position of each foot is determined from the information received from the light sensors included with the linear array 80 of infrared temperature sensors 92 which traverses the bottom of each foot several times. Because the pressure of a patient's foot blocks ambient light from passing through the holes in the grid, light to the light sensors will be blocked while light will pass through the uncovered holes in the grid. This provides a light picture of the position and size of a patient's foot on the grid. Once the computer receiving the information on foot size and position from the light sensors in the linear array 80 determines the position of the foot on the grid 90, the temperature sensors measure the temperature at preselected sites on the bottom or plantar aspects of both feet. Alternatively, the position and size of a patient's foot on the grid may be located by creating a temperature picture of the patient's foot using techniques well known to those of ordinary skill in the art.

The device 10, 110 will alert the user if there is an abnormally high skin temperature gradient between the plantar, dorsal, lateral, or medial aspects of the contralateral feet. The presence of such a significant skin temperature gradient may be indicative of a pathologic inflammation or possible tissue damage at that location on the user's foot. Such inflammation or tissue damage might be an indicator of a predisposition to further tissue breakdown in the foot and/or significant morbidity which, if left untreated, may lead to an amputation or, in extreme cases, death.

As shown in FIG. 1 and FIG. 1A, the apparatus of the present invention 10, 110 is built around a platform assembly 20, 120 that is placed on a hard surface (not shown). The first 25 and second surfaces 27 are used to guide the initial placement of the patient's feet on the platform assembly 20. These surfaces assist the patient in placing his/her feet reproducibly and accurately on the platform assembly 20. For patients with unusually shaped or deformed feet, custom fabricated foot placement surfaces or replaceable inserts may be used with the grid plate 90.

In the preferred embodiment shown in FIG. 1, light sensors are used to determine the location of the user's feet on the platform 20. This location information is then used to select the particular holes 92 in the grid 90 through which the infrared temperature sensors 82 can measure the foot sole skin temperature.

The infrared temperature sensors 82, provide an electrical signal representative of a skin temperature level at the predetermined location of a hole 92 in the grid 90. These electrical signals may then be displayed as either Fahrenheit or Celsius temperature readings to the patient or a medical professional.

If desired a liquid crystal display 50, 150 can either show the actual temperature values measured by one or more infrared temperature sensors 82 and/or alert the user that a difference in temperature may exist between two sensor sites. Alternatively, the temperature readings or warnings about possibly dangerous temperature differences may be conveyed audibly to the user through one or more speakers 55, 155.

As shown in FIG. 1A, it has also been found that the utility of the apparatus 110 for monitoring the temperature of the plantar aspects of the human foot can be expanded to measure other vital health information through the use of a variety of different enhancements. Specifically, the apparatus of the present invention can easily be modified to also measure the weight of the patient by placing pressure sensitive transducers (not shown) in the platform assembly 20. The measurement of weight is important because fluctuations in weight may be significant to patients in the different stages of congestive heart failure. Such sudden weight change usually signifies a dangerous buildup of water or liquid retention. The need to monitor fluctuations in weight is particularly important for diabetics who are prone to suffer from congestive heart failure. Thus, it is desirable for diabetics that the foot temperature variations and body weight changes be quantified and displayed on a daily basis. Selection of the health information displayed is facilitated by the use of easily accessible buttons 57 or a keypad 59 as shown in FIG. 1A.

If desired, body weight may be measured with the apparatus using a force or pressure transducer in the same way that force or pressure transducers are used in standard bathroom scales. The liquid crystal display 150 may be used for the display of body weight.

It has also been found that the preferred embodiment of the apparatus 110 of the present invention may be further enhanced by the addition of still other medical condition monitoring systems well known to those of ordinary skill in the art. Such other medical condition monitoring systems may measure blood glucose levels with a finger pin stick system 170, an arm blood pressure cuff and pulse counter 174, or a red light and light sensor 176 for transcutaneous monitoring, clipped on the end of a finger to measure blood oxygen levels. Present technology enables the measurement of blood glucose levels and blood oxygen levels using a variety of techniques including lasers, infrared percutaneous readings or assessment of blood glucose levels using the patient's saliva. Blood pressure and pulse may even be sensed on the foot or lower leg with an ankle cuff or toe cuff 178.

Figure 3:
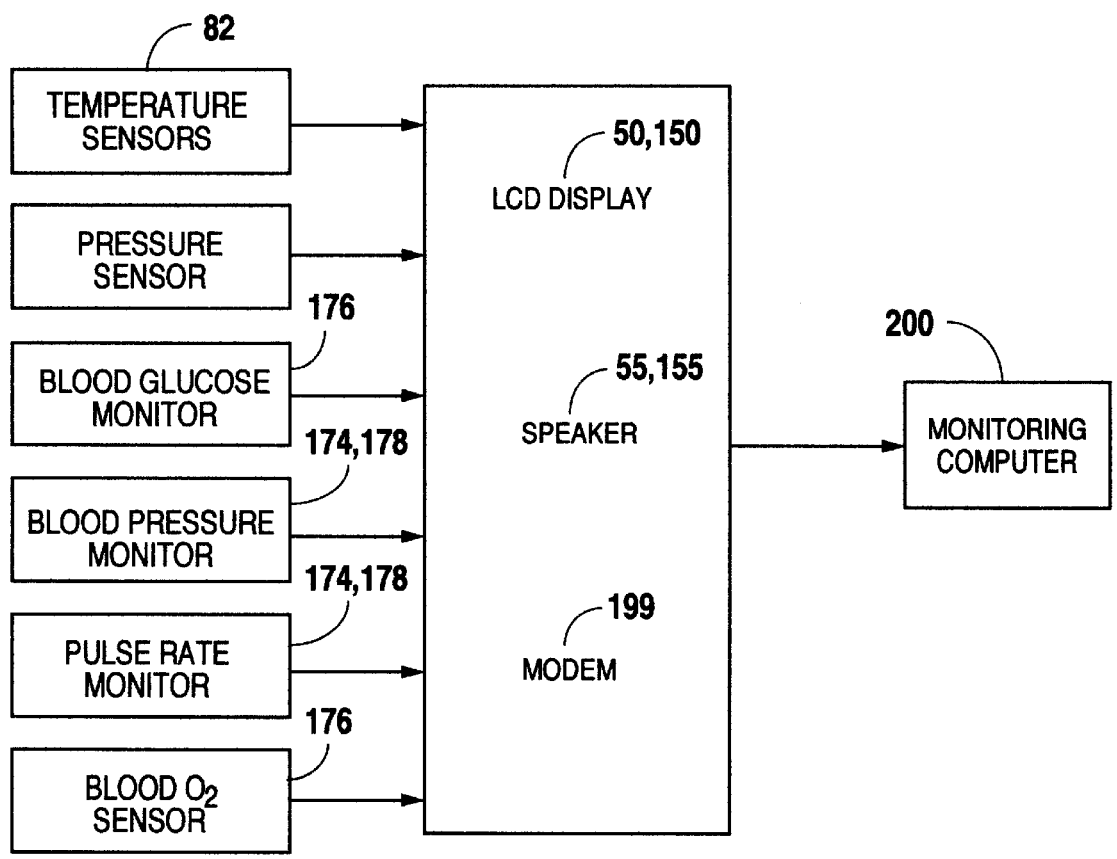
FIG. 3 is a schematic diagram of the interrelationship of the main components of the present invention.

As shown in FIG. 3, once the vital health information has been obtained by the apparatus 10, 110 of the present invention, it may be stored internally where it can be compared with prior data to inform the user of noticeable trends in changes of weight or temperature and, if necessary, provide an alarm signal. Alternatively, the information may be sent to a central computer 200 using a modem 199 connected to a standard telephone system, the internet, cell phone, or other wireless communication means. The central computer 200 monitors the measurements of vital health information taken by the device 10, 110 and thereby allows such measurements to be taken by patients in the comfort of their own home.

Operation

The embodiment of the present invention illustrated in FIGS. 1, 1A, and 2 is designed to be utilized if the patient is standing. A key aspect of the present invention is to assure that the location of the patient's feet are properly located with respect to the array of infrared temperature sensors 82 located in the platform assembly 20. Specifically, the computer receiving the sensed skin temperature information must be able to tie a location on the bottom of the patient's foot to the sensed temperature.

In a preferred embodiment the data collected by the apparatus 10, 110 will be marked with an indication of the date and time the skin temperature readings were taken. All sensed information to include the date and time that readings were taken may be stored at the device 10, 110 itself or transmitted to a remote location by standard telephone wires or wireless means where it may be stored and later analyzed.

If the data is transmitted to a database at a remote location, it would then be possible for a health care professional to monitor the data and determine if a significant change has occurred in the contralateral temperatures of a user's lower extremities, the user's weight, or the user's blood pressure.

The embodiment of the invention illustrated in FIG. 4 is designed to be utilized if the person is seated or reclining. The device will monitor the temperature of the skin surface based upon the location data received from an array of pressure sensors contained within the blanket 210. FIG. 5 illustrates the embodiment of the invention which is designed to be utilized if the apparatus is to be positioned around an extremity wherein the temperature sensors will simply measure the temperature of the entire skin surface inside the wrap. Such system is particularly helpful for monitoring the healing of a small bone break or a sprain.

The apparatus and method of the present invention may also provide the foundation for a method of operating a health information monitoring business. Specifically, the sensed vital health information could be sent to a data storage facility and compared with past data or predetermined levels of vital health information. If this comparison yields an indication of a condition which is predictive of near term or future health problems, a health care professional may call the patient and recommend a consultation or treatment which may cure a nascent condition before life or limb-threatening symptoms are experienced. Such a vital health information monitoring system could be required for use by designated employees of an employer to reduce lost time maladies. Further, such a vital health information monitoring system could also be required for use by life or health insurance companies to provide a basis for reassessing the risk that the insurance company will have to pay for the health care costs associated with an illness or malady or the face amount of a life insurance policy on the death of the insured. Such risk reassessment could be used to tailor premium rates to the health of individual insureds.

It will be understood by those of ordinary skill in the art that while the apparatus and method of the present invention has been described with respect to its preferred embodiment, those of ordinary skill in the art will understand the numerous other embodiments of this invention may be possible without departing from the foregoing teachings. Such other embodiments shall be included within the scope and meaning of the appended claims.

What is claimed is:

1. "An apparatus for monitoring the temperature of the plantar aspects of the foot of a human being, said device comprising: a grid having a plurality of holes therein at predetermined locations; a movable array of light sensors and skin temperature sensors; said movable array of light sensors and skin temperature sensors constructed and arranged to travel under said grid and produce signals representative of the location of the feet and the skin temperatures on the plantar aspects of feet through said holes in said grid; computer means for receiving said signals representative of the location of the feet and the skin temperatures on the plantar aspects of the feet; said computer means constructed and arranged to both determine the position of the feet with respect to said holes in said grid using said signals representative of the location of the feet and the temperatures on the plantar aspects of the feet and selecting and recording sensed skin temperatures from certain of such holes; and means for displaying an output of said recorded skin temperatures."

2. The apparatus as defined in claim 1 further including means for generating a warning if a temperature exceeding a predetermined level as between two or more similar locations on the feet or adjacent sites on one foot is sensed.

3. The apparatus as defined in claim 1 wherein said output of recorded temperatures is a visual output.

4. The apparatus as defined in claim 3 wherein said visual output is a liquid crystal display.

5. The apparatus as defined in claim 1 wherein said output of sensed temperatures is an audio output.

6. The apparatus as defined in claim 1 further including means for sensing and displaying the weight of the human being.

7. The apparatus as defined in claim 1 further including means for sensing and displaying the blood pressure of the human being.

8. The apparatus as defined in claim 7 further including means for transmitting the sensed blood pressure to a remote location.

9. The apparatus as defined in claim 1 further including means for sensing and displaying the pulse rate of the human being.

10. The apparatus as defined in claim 9 further including means for transmitting the sensed pulse rate to a remote location.

11. The apparatus as defined in claim 1 further including means for sensing and displaying the blood glucose levels of the human being.

12. The apparatus as defined in claim 11 further including means for transmitting the sensed blood glucose level to a remote location.

13. The apparatus as defined in claim 1 further including means for sensing and displaying the blood oxygen levels of the human being.

14. The apparatus as defined in claim 13 further including means for transmitting the sensed blood oxygen level to a remote location.

15. The apparatus as defined in claim 1 further including a modem for transmitting the recorded foot temperatures to a remote location.

16. A system for monitoring the temperatures of the plantar aspects of the feet of a plurality of patients, said system comprising:
a grid having a plurality of holes formed therein, said holes being located at predetermined locations:
a movable array of light sensors;
said movable array of light sensors constructed and arranged to travel under said grid and produce signals indicating the location of the patient's feet through said holes in said grid;
a movable array of skin temperature sensors;
said movable array of skin temperature sensors constructed and arranged to travel under said grid and produce signals representative of the skin temperatures on the plantar aspects of the patient's feet through said holes in said grid;
a computer for receiving said signals representative of said location of the patient's feet and said skin temperatures on the plantar aspects of the patient's feet;
said computer constructed and arranged to both determine the position of patients' feet with respect to said holes in said grid using said signals representative of said location of the patient's feet and said skin temperatures on the plantar aspects of the feet and selecting certain of said holes for recording sensed temperatures;
means for converting said signals generated by said heat sensitive probes into an output expressed in terms of temperature;
means for sending said signals to a remote location;
means for storing and analyzing said signals at said remote location;
whereby the temperatures of the feet of a plurality of human beings may be monitored at said remote location.

17. The system as defined in claim 16 wherein said means for sending said signals to a remote location is a telephone modem.

18. The system as defined in claim 16 wherein said means for sending said signals to a remote location is a wireless means.

19. The system as defined in claim 16 further including means for generating a warning if a temperature difference exceeding a predetermined level as between two or more of said probes is sensed.

20. The system as defined in claim 19 further including means for generation of an audio warning.

21. The system as defined in claim 16 further including a visual display of sensed temperatures.

22. The system as defined in claim 16 further including means for sensing and displaying the weight of a patient.

23. The system as defined in claim 16 further including means for sensing and displaying the blood pressure of a patient.

24. The system as defined in claim 16 further including means for sensing and displaying the pulse rate of a patient.

25. The system as defined in claim 16 further including means for sensing and displaying the blood glucose levels of a patient.

26. The system as defined in claim 16 further including means for sensing and displaying the blood oxygen levels of a patient.

27. The system as defined in claims 16, 22, 23, 24, 25, and 26 further including means for storing the sensed information along with the date and time when the information was sensed.

28. A health monitoring system comprising:
a grid having a plurality of holes therein at predetermined locations, said grid including a portion for the bottom of a patient's left foot and a portion for the bottom of a patient's right foot;
a movable, substantially linear array of light sensors and infrared temperature sensors:
said movable, substantially linear array of light sensors and infrared temperature sensors, constructed and arranged to travel under said grid and produce signals representative of foot location and skin temperatures on the bottom of the patient's feet covering said holes;
at least one guide per foot for enabling registration of the physical position of a patient's foot with respect to said grid;
means for receiving and displaying the foot location signals using said movable, substantially linear array of light sensors
means for receiving and displaying the skin temperatures on the bottom of the patient's feet using said movable, substantially linear array of infrared sensors.

29. A method for monitoring the temperature at predetermined locations on the feet of a human being, said method comprising the steps of: locating the position of the feet on the top surface of a grid plate; sensing the skin temperatures of the predetermined locations on the bottom of the feet beneath the bottom surface of said grid plate; wherein the step of locating the position of the feet on a grid plate further includes, sensing the position of the feet on said grid plate using an array of light sensors; whereby said light sensors are constructed and arranged to detect light shining through holes in said grid plate.

30. A method for monitoring the temperature at predetermined locations on the feet of a human being, said method comprising the steps of: locating the position of the feet on the top surface of a grid plate; and sensing the skin temperatures of the predetermined locations on the bottom of the feet beneath the bottom surface of said grid plate; wherein the step of sensing the skin temperatures of the predetermined locations on the bottom of the feet further includes: sensing the skin temperatures at predetermined locations on the bottom of a patient's feet using an array of temperature sensors; and whereby said temperature sensors are constructed and arranged to measure skin temperature through said holes in said grid plate.

* * * * *